US008886312B2

(12) United States Patent
Yu et al.

(10) Patent No.: US 8,886,312 B2
(45) Date of Patent: Nov. 11, 2014

(54) APPARATUSES AND METHODS USING THE ROLE OF VENTRICULAR ELECTRICAL DELAY TO PREDICT LEFT VENTRICULAR REMODELING WITH CARDIAC RESYNCHRONIZATION THERAPY

(75) Inventors: Yinghong Yu, Shoreview, MN (US); Shibaji Shome, Arden Hills, MN (US); Dan Li, Shoreview, MN (US); Michael Gold, Daniel Island, SC (US); Jagmeet Singh, Newton, MA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 53 days.

(21) Appl. No.: 13/542,261

(22) Filed: Jul. 5, 2012

(65) Prior Publication Data
US 2013/0172954 A1 Jul. 4, 2013

Related U.S. Application Data

(60) Provisional application No. 61/507,550, filed on Jul. 13, 2011, provisional application No. 61/527,910, filed on Aug. 26, 2011.

(51) Int. Cl.
*A61B 5/0456* (2006.01)
*A61B 5/0472* (2006.01)
*A61N 1/365* (2006.01)
*A61B 5/00* (2006.01)
*A61B 5/042* (2006.01)
*A61N 1/368* (2006.01)

(52) U.S. Cl.
CPC .......... *A61N 1/36592* (2013.01); *A61B 5/0472* (2013.01); *A61B 5/686* (2013.01); *A61B 5/0456* (2013.01); *A61B 5/0006* (2013.01); *A61B 5/0422* (2013.01); *A61N 1/3684* (2013.01)

USPC ............................................. 607/25; 600/521

(58) Field of Classification Search
None
See application file for complete search history.

(56) References Cited

U.S. PATENT DOCUMENTS

| 5,527,347 A | 6/1996 | Shelton et al. |
| 6,144,880 A | 11/2000 | Ding et al. |

(Continued)

FOREIGN PATENT DOCUMENTS

| WO | WO-2013009563 A1 | 1/2013 |
| WO | WO-2013016119 A1 | 1/2013 |

OTHER PUBLICATIONS

"U.S. Appl. No. 13/552,996, Response filed Aug. 26, 2013 to Restriction Requirement mailed Jul. 25, 2013", 12 pgs.

(Continued)

*Primary Examiner* — Michael Kahelin
(74) *Attorney, Agent, or Firm* — Schwegman Lundberg & Woessner, P.A.

(57) ABSTRACT

A system comprises a cardiac signal sensing circuit and a processor circuit. The cardiac signal sensing circuit is configured to sense a cardiac signal segment using a set of electrodes connectable to the cardiac signal sensing circuit. The processor circuit is communicatively coupled to the cardiac signal sensing circuit and includes a peak detector circuit. The peak detector circuit is configured to identify, in the cardiac signal segment, a fiducial indicative of ventricular activation that is local to at least one electrode of the first set of electrodes. The fiducial includes a first large positive or negative peak greater than a specified percentage of a maximum peak of the first cardiac signal segment. The processor circuit is configured to provide an indication of local ventricular activation to at least one of a user or process.

20 Claims, 5 Drawing Sheets

(56) References Cited

U.S. PATENT DOCUMENTS

| | | |
|---|---|---|
| 6,370,427 B1 | 4/2002 | Alt et al. |
| 6,597,951 B2 | 7/2003 | Kramer et al. |
| 6,622,040 B2 | 9/2003 | Ding et al. |
| 6,671,549 B2 | 12/2003 | Van Dam et al. |
| 6,751,504 B2 | 6/2004 | Fishler |
| 6,766,189 B2 | 7/2004 | Yu et al. |
| 6,804,555 B2 | 10/2004 | Warkentin |
| 6,999,815 B2 | 2/2006 | Ding et al. |
| 7,043,301 B1 | 5/2006 | Kroll et al. |
| 7,103,412 B1 | 9/2006 | Kroll |
| 7,139,610 B2 | 11/2006 | Ferek-Petric |
| 7,181,285 B2 | 2/2007 | Lindh et al. |
| 7,209,785 B2 * | 4/2007 | Kim et al. ............... 607/5 |
| 7,231,248 B2 | 6/2007 | Kramer et al. |
| 7,313,433 B2 | 12/2007 | Yu et al. |
| 7,424,324 B2 | 9/2008 | Ding et al. |
| 7,546,162 B2 | 6/2009 | Ding et al. |
| 7,558,626 B2 | 7/2009 | Corbucci |
| 7,590,446 B1 | 9/2009 | Min et al. |
| 7,630,764 B2 | 12/2009 | Ding et al. |
| 7,912,544 B1 | 3/2011 | Min et al. |
| 2002/0077559 A1 | 6/2002 | Ding et al. |
| 2005/0149138 A1 | 7/2005 | Min et al. |
| 2006/0241703 A1 | 10/2006 | Ding et al. |
| 2007/0208386 A1 | 9/2007 | Kramer et al. |
| 2008/0004665 A1 | 1/2008 | McCabe et al. |
| 2008/0058656 A1 | 3/2008 | Costello et al. |
| 2008/0097542 A1 | 4/2008 | Yu et al. |
| 2008/0177344 A1 * | 7/2008 | Maskara et al. ............ 607/25 |
| 2008/0269822 A1 | 10/2008 | Ljungstrom et al. |
| 2009/0112276 A1 | 4/2009 | Yu et al. |
| 2009/0149904 A1 | 6/2009 | Perschbacher et al. |
| 2009/0299203 A1 | 12/2009 | De Voir et al. |
| 2009/0306732 A1 * | 12/2009 | Rosenberg et al. ............ 607/9 |
| 2010/0069988 A1 | 3/2010 | Ding et al. |
| 2013/0190636 A1 | 7/2013 | Shome et al. |

OTHER PUBLICATIONS

"U.S. Appl. No. 13/552,996, Restriction Requirement mailed Jul. 25, 2013", 7 pgs.

"International Application Serial No. PCT/US2012/045543, Search Report mailed Oct. 17, 2012", 3 pgs.

"International Application Serial No. PCT/US2012/045543, Written Opinion mailed Oct. 17, 2012", 6 pgs.

"International Application Serial No. PCT/US2012/047335, Search Report mailed Oct. 17, 2012", 4 pgs.

"International Application Serial No. PCT/US2012/047335, Written Opinion mailed Oct. 17, 2012", 7 pgs.

"U.S. Appl. No. 13/552,996, Non Final Office Action mailed Nov. 1, 2013", 7 pgs.

* cited by examiner

APPARATUSES AND METHODS USING THE ROLE OF VENTRICULAR ELECTRICAL DELAY TO PREDICT LEFT VENTRICULAR REMODELING WITH CARDIAC RESYNCHRONIZATION THERAPY

CLAIM OF PRIORITY

This application claims the benefit of priority under 35 U.S.C. §119(e) of Yinghong Yu, U.S. Provisional Patent Application Ser. No. 61/507,550, filed on Jul. 13, 2011, and also the benefit of priority under 35 U.S.C. §119(e) of Yu et al., U.S. Provisional Patent Application Ser. No. 61/527,910, filed on Aug. 26, 2011, the benefit of priority of each of which is claimed hereby, and each of which are incorporated by reference herein in their entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Medical devices also include ambulatory or wearable medical devices (WMDs) such as wearable cardioverter defibrillators (WCDs). WCDs are monitors that include surface electrodes. The surface electrodes are arranged to provide one or both of monitoring surface electrocardiograms (ECGs) and delivering cardioverter and defibrillator shock therapy. Some medical devices include one or more sensors to monitor different physiologic aspects of the patient. For example, the devices may derive measurements associated with a cardiac depolarization of the patient. Such measurements can provide useful information concerning the cardiac health of the patient.

By monitoring cardiac signals indicative of expansions or contractions, IMDs can detect abnormally slow heart rate, or bradycardia. In response to an abnormally slow heart rate some CFM devices deliver electrical pacing stimulation energy to induce cardiac depolarization and contraction. The pacing stimulation energy is delivered to provide a depolarization rate that improves hemodynamic function of the patient. Delivery of pacing therapy should be optimized to ensure therapy delivery and yet avoid unnecessary stress on the heart and unnecessary reduction of battery life. Optimal selection of the site for delivery of the pacing therapy can be part of pacing therapy optimization. Optimal site selection can lead to optimized use of pacing energy and to improved hemodynamic function of the patient or subject.

Monitoring cardiac signals may also detect abnormalities in the synchronization of contractions between the left and right sides of the heart. These abnormalities are sometimes treated with an IMD that delivers cardiac resynchronization therapy (CRT).

OVERVIEW

This document relates generally to systems, devices, and methods that provide one or both of diagnostic monitoring and electrical device-based therapy to the heart of a patient or subject. In particular it relates to, systems, devices, and methods that monitor local ventricular activation of the heart.

A system example includes a cardiac signal sensing circuit and a processor circuit. The cardiac signal sensing circuit is configured to sense a cardiac signal segment using a set of electrodes connectable to the cardiac signal sensing circuit. The processor circuit is communicatively coupled to the cardiac signal sensing circuit and includes a peak detector circuit. The peak detector circuit is configured to identify, in the cardiac signal segment, a fiducial indicative of ventricular activation that is local to at least one electrode of the first set of electrodes. The fiducial includes a first large positive or negative peak greater than a specified percentage of a maximum peak of the first cardiac signal segment. The processor circuit is configured to provide an indication of local ventricular activation to at least one of a user or process.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

A medical device (e.g., an IMD or a wearable device) can include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
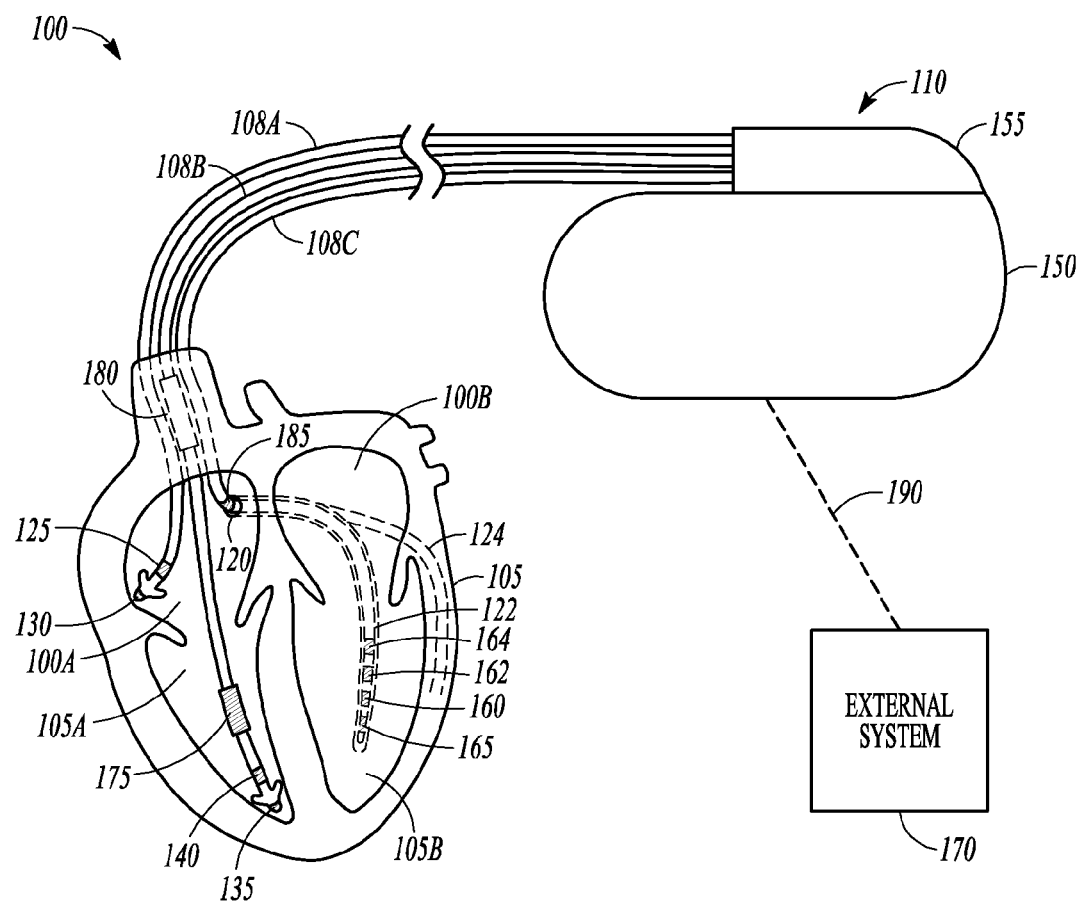
FIG. 1 is an illustration of an example of portions of a system that includes an IMD.

FIG. 1 is an illustration of an example of portions of a system that uses an IMD 110 or other ambulatory medical device that can be capable of moving about with the subject, such as chronically during activities of daily living. Examples of IMD 110 include, without limitation, a pacemaker, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 can be coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 can include a third cardiac lead 108C attached to the IMD 110 through the header 155. The third cardiac lead 108C includes electrodes 160, 162, 164, and 165 placed in a coronary vein lying epicardially on the left ventricle (LV) 105B via the coronary vein. The third cardiac lead 108C may include anywhere from two to eight electrodes, and may include a ring electrode 185 positioned near the coronary sinus (CS) 120.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. The combination of electrodes used in shock therapy is sometimes called a shock channel or shock vector because the combination of electrodes can result in delivery of therapy in a particular direction. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, an IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). The present methods and systems will work in a variety of configurations and with a variety of electrodes. Other forms of electrodes include meshes and patches which can be applied to portions of heart 105 or which can be implanted in other areas of the body to help "steer" electrical currents produced by IMD 110.

Figure 2:
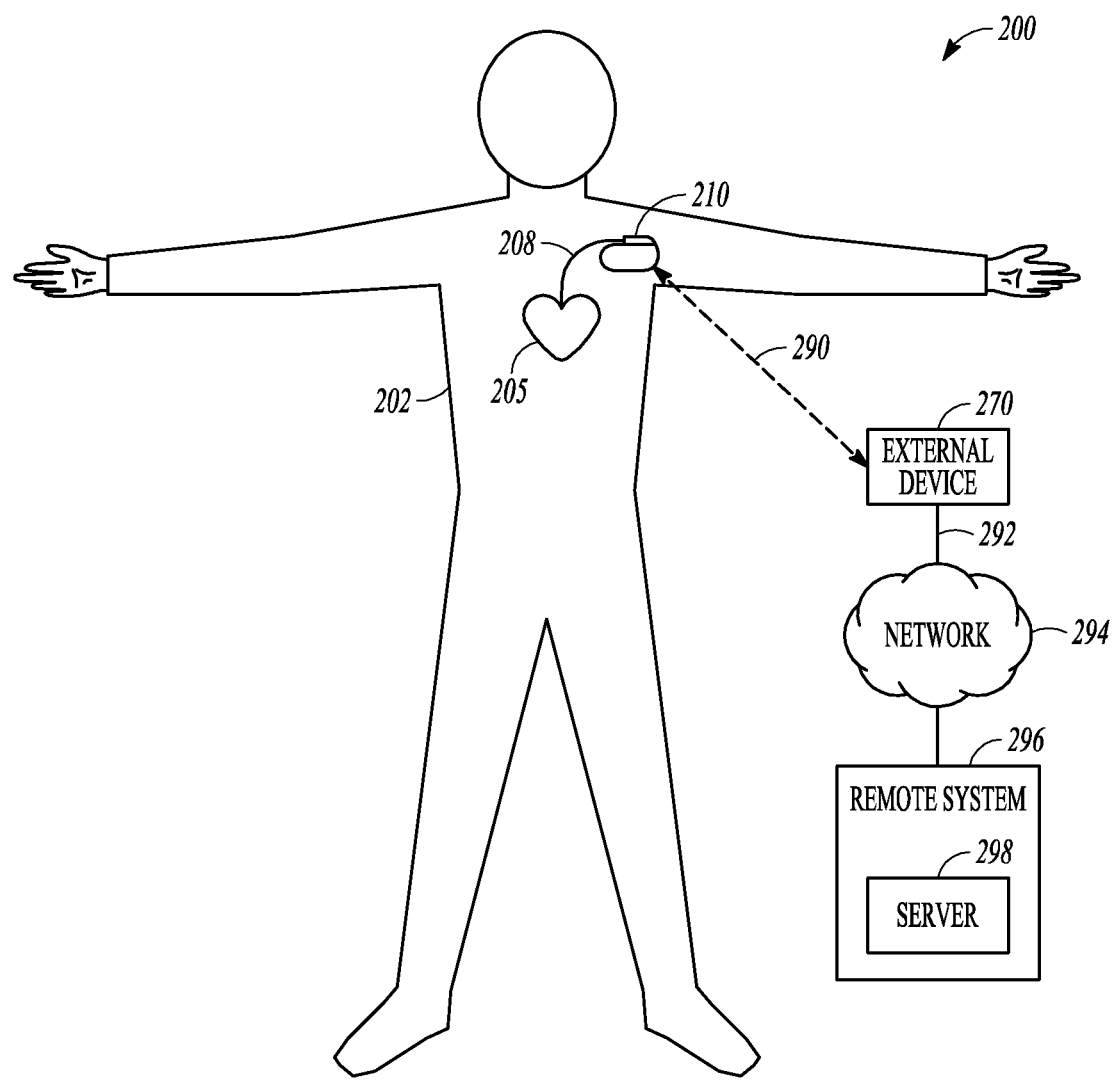
FIG. 2 is an illustration of portions of another system that uses an IMD.

FIG. 2 is an illustration of portions of another system 200 that uses an IMD 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicated via the network using a link 292 that may be wired or wireless. In some examples, the remote system 296 provides patient management functions and may include one or more servers 298 to perform the functions.

A medical device can monitor electrical activity of the heart of a patient. For example, a wearable medical device may include surface electrodes (e.g., electrodes for skin contact) to sense a cardiac signal such as an electrocardiograph (ECG) of the patient. An IMD may include implantable electrodes to sense a cardiac signal such as an internal electrogram of the patient. Measurements of the cardiac signal can provide useful information concerning the patient's cardiac health.

A sensed cardiac signal can include a QRS complex. The QRS complex is a waveform produced by depolarization of the ventricles and is composed of a Q-wave, an R-wave, and an S-wave. The interval from the onset of the Q-wave to the termination of the S-wave is sometimes called the QRS width or QRS duration. The time duration of the QRS complex can indicate the efficacy of the cardiac contraction. This can be useful to detect proper beat-to-beat capture of the heart by a device that provides pacing stimulation therapy. A shorter QRS complex would indicate proper capture and a longer QRS complex would indicate a less effective contraction.

Patients with a wide QRS complex can also be used to identify candidates to receive a CRT device. Most HF patients with wide QRS have left ventricular conduction delays (LBBB). A CRT device reestablishes electrical synchrony by pre-exciting the delayed LV area to achieve more synchronous electrical activation and thus contraction within the left ventricle. CRT may include bi-ventricular pacing or only left ventricular pacing.

Identifying patients that have wide QRS complexes can lead to improved therapy for the patients, such as by implanting the patients with a medical device can deliver cardiac resynchronization therapy. Early identification of patients who have wide QRS complexes may improve mortality of patient with cardiac disease. Methods and systems to identify whether a patient is a responder for cardiac resynchronization therapy by using width of the QRS complex can be found in Ding et al., "Identifying Heart Failure Patients Suitable for Resynchronization Therapy Using QRS complex width from an Intracardiac Electrogram," U.S. Pat. No. 7,424,324, filed May 20, 2005, which is incorporated herein by reference in its entirety.

However, the duration of the QRS complex reflects the conduction system condition of both ventricles. A measure of local ventricular activation may provide additional information about the subject's ventricular depolarization. For instance, the Q-LV interval is the time duration from the onset of the Q-wave to the time of local activity at the site of the LV electrode. Thus, the Q-LV interval reflects the time that it takes for a ventricular depolarization wavefront or activation wavefront to reach the local LV electrode site. Similarly, the Q-RV interval reflects the time that it takes for a ventricular activation wavefront to reach the RV electrode site.

Providing pacing energy at an improper pacing site or location can lead to slow activation of myocardial tissue. Thus, it is desirable to have an IMD or other medical device that can automatically run tests to determine the best pacing site or sites, and either propose to the caregiver that these sites be used to provide the pacing therapy or automatically initiate delivery of pacing therapy to a determined optimal pacing site. Additionally, it may be desirable to have an IMD or other medical device that can automatically run tests to identify candidates for CRT therapy. Knowledge of the Q-LV interval can provide information regarding optimum lead placement in the LV in addition to the QRS width. The Q-RV interval can be used to guide placement of leads and electrodes in the right ventricle (RV). Additionally, knowledge of the Q-LV interval may also be useful in identifying patients that most likely to respond well to CRT. Consequently, measurements of the Q-LV time interval provide useful information concerning a patient's cardiac health.

Figure 3:
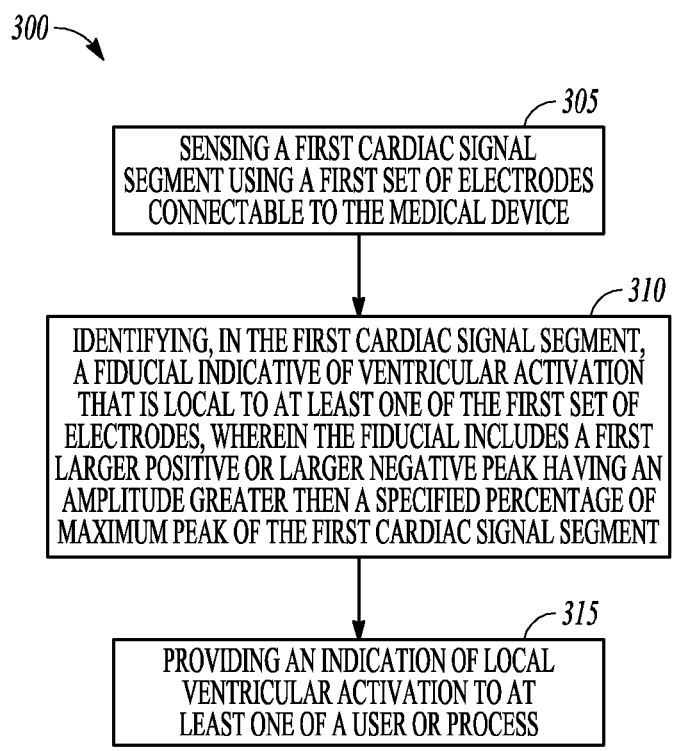
FIG. 3 shows a flow diagram of an example of a method of operating a medical device to measure local activation of a ventricle

FIG. 3 shows a flow diagram of an example of a method 300 of operating a medical device to measure local activation of a ventricle. At block 305, a first cardiac signal segment is sensed using a first set of electrodes connectable to the medical device. Typically, the electrodes are implantable, such as by being incorporated into one or more implantable leads. The first cardiac signal segment is sensed over a cardiac cycle, or at least a portion of a cardiac cycle that includes a QRS complex.

At block 310, a fiducial is identified in the first cardiac signal segment by the medical device. The fiducial is indicative of ventricular activation that is local to at least one of the first set of electrodes. In certain examples, activation is local when the activation occurs within ten millimeters (10 mm) of an electrode or set of electrodes. The fiducial includes a first large positive or large negative peak having an amplitude greater than a specified percentage of a maximum peak amplitude of the first cardiac signal segment. In certain examples, the fiducial peak includes an amplitude greater than, equal to, or about equal to 50% of the maximum peak amplitude in the first cardiac signal segment.

Figure 4:
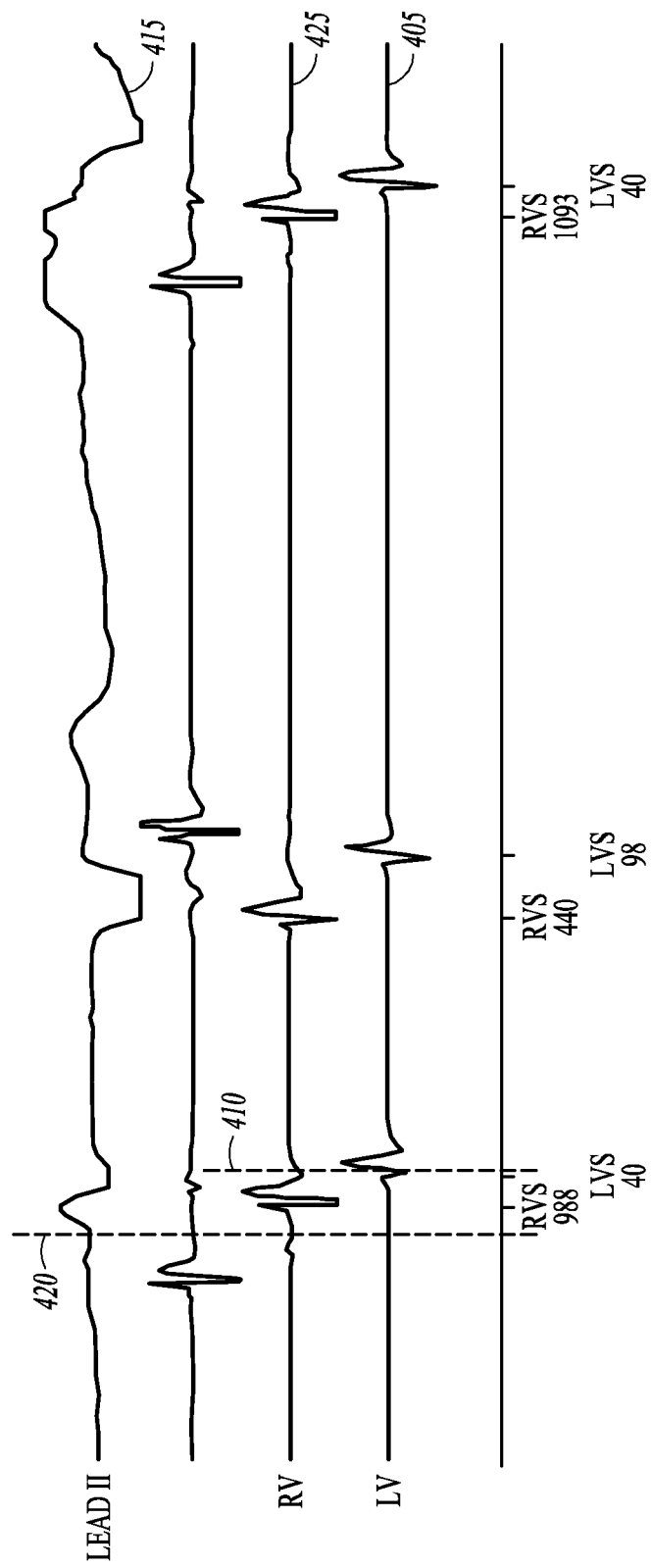
FIG. 4 shows an example of waveforms indicative of local ventricular activation.

FIG. 4 shows an example of waveforms indicative of local ventricular activation. Waveform 405 illustrates a cardiac signal sensed using implantable electrodes to obtain an intracardiac electrogram or egram. The second vertical line 410 indicates an example of a fiducial in waveform 405 that is representative of local cardiac activation. The fiducial corresponds to a negative peak that is more than 50% of the largest peak in the waveform.

Returning to FIG. 3, at block 315 an indication of local ventricular activation is provided to at least one of a user or process. The process that can receive the indication may be executing in the medical device or a separate device. The indication can be presented to a user on a display incorporated into the medical device or included in a separate device. In some examples, the indication is related to the subject being a candidate for CRT. In some examples, the indication is related to an optimum location for placement of an implantable lead or electrode.

According to some examples, the indication includes a time duration or time interval associated with the fiducial. In some examples, the time duration includes a time interval from the onset of a Q-wave to a fiducial representative of local ventricular activation.

A second cardiac signal segment can be sensed by the medical device using a second set of electrodes. The second cardiac signal can be sensed during the same cardiac cycle as the fiducial representative of local ventricular activation identified in the first cardiac signal segment. The second cardiac signal segment includes a QRS complex, and an onset of the Q-wave is identified in the QRS complex. Descriptions of using a device to identify the Q-wave can be found in the previously identified U.S. Pat. No. 7,424,324. In the method 300, the medical device can determine the time duration between the onset of the Q-wave and the fiducial of the first cardiac signal segment, and provide the determined time duration to at least one of a user or process.

In FIG. 4, the top waveform 415 illustrates a cardiac signal that is sensed using surface electrodes (e.g., an ECG). The first vertical line corresponds to the onset of the Q-wave. Because the second vertical line 410 corresponds to LV local activation, the interval between the vertical lines is representative of the Q-LV interval, which can be the time duration determined by the medical device. The Q-LV interval is the time from earliest activation of a site in the ventricle (the Q-wave onset) to the time of local LV activity (the LV time) measured using the electrodes.

Also shown in FIG. 4, is a waveform 425 that illustrates a cardiac signal sensed in the RV using implantable electrodes. The fiducial in the first cardiac signal segment can indicate RV activation that is local to at least one electrode of the first set of electrodes. The time duration determined by the medical device can be the time duration between the onset of the Q-wave and RV activation. This Q-RV interval is the time from the earliest activation of a site in the ventricle (the Q-wave onset) to the time of local RV activity.

In some examples, a first cardiac signal segment can be sensed using electrodes implanted in or near the LV, and a second cardiac signal segment can sensed using electrodes implanted in or near the RV. The fiducial in the first cardiac signal segment can indicate LV local activation, and the medical device can identify a fiducial in the second cardiac signal segment that indicates RV local activation. The fiducial in the second cardiac signal segment can include a first large positive or large negative peak having an amplitude greater than a specified percentage of a maximum peak amplitude of the second cardiac signal segment. The percentage can be the same percentage or fraction used to identify the fiducial in the first segment or can be a different percentage or fraction. The time duration determined by the medical device can be the time duration between the second fiducial indicative of RV local activation and the first fiducial indicative of LV local activation. This RV-LV interval can be the time from RV local activity at the second set of electrodes to the time of LV local activity at the first set of electrodes.

Examples have been described of determining timing intervals that include local activation time. These intervals include the Q-LV interval, the Q-RV interval and the RV-LV interval. One of skill in the art would understand, upon reading this document, that the method can be applied to determine other intervals that include local activation time of the myocardium.

Figure 5:
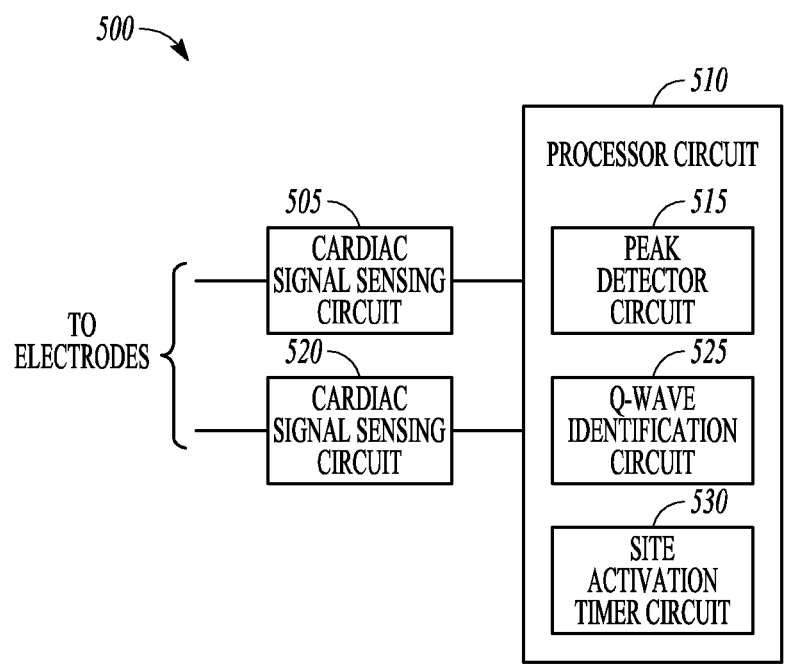
FIG. 5 shows a block diagram of an example of a medical system to measure local activation of a ventricle.

FIG. 5 shows a block diagram of an example of a medical system to measure local activation of a ventricle. The system 500 includes a first cardiac signal sensing circuit 505 and a processor circuit 510. The first cardiac signal sensing circuit 505 senses a first cardiac signal segment using a first set of electrodes connectable to the first cardiac signal sensing circuit 505. In some examples, one or more electrodes of the set of electrodes can be incorporated into an implantable lead or incorporated into a housing or header of an implantable device. The cardiac signal segment includes a sensed cardiac cycle.

The processor circuit 510 is communicatively coupled to the cardiac signal sensing circuit 505. The communicative coupling allows the processor circuit 510 to receive electrical signals from the cardiac signal sensing circuit 505 even though there may be intervening circuitry. The cardiac signal sensing circuit 505 may be included in a device separate from the processor circuit 510 and the intervening circuitry may include one or more communication circuits to communicate information wirelessly between the cardiac signal sensing circuit 505 and processor circuit 510. The processor circuit 510 can be an application specific integrated circuit (ASIC), a microprocessor, a digital signal processor, or other type of processor, interpreting or executing instructions in software modules or firmware modules. The processor circuit 510 can include other circuits or sub-circuits to perform the functions described. These circuits may include software, hardware, firmware or any combination thereof. Multiple functions can be performed in one or more of the circuits as desired.

The processor circuit 510 includes a peak detector circuit 515 that identifies a fiducial in the first cardiac signal segment. The fiducial includes a first large positive or negative peak greater than a specified percentage of a maximum peak amplitude of the first cardiac signal segment, and the fiducial is indicative of ventricular activation that is local to at least one electrode of the first set of electrodes. The processor circuit 510 provides an indication of local ventricular activation to at least one of a user or process.

The indication can include a measure of local ventricular activation, or a measure of a time interval that includes the local ventricular activation. In some examples, the processor circuit 510 generates an indication of prospective responsiveness to cardiac resynchronization therapy (CRT) based on the determined time duration or time interval. In some examples, the processor circuit 510 generates an indication of optimality of the placement of at least one electrode of the first set of electrodes based on the measured time duration or time interval.

In some examples, the system 500 includes a second cardiac signal sensing circuit 520 that senses a second cardiac signal segment using a second set of electrodes. The second set of electrodes can include at least one electrode that is different from the first set of electrodes. Thus, the second set of electrodes can share an anode or a cathode with the first set of electrodes, and yet can provide directional informational about the activation wavefront.

The second cardiac signal segment includes a QRS complex that is sensed during the same cardiac cycle as the cardiac cycle of the fiducial in the first cardiac signal segment. The processor circuit 510 includes a Q-wave identification circuit 525 that identifies an onset of a Q-wave in the QRS complex. In some examples, the Q-wave identification circuit 525 identifies a Q-wave using one or more of the methods described in the previously mentioned U.S. Pat. No. 7,424,324. The processor circuit 510 includes a site activation timer circuit 530 that determines a time duration between onset of the Q-wave and the identified fiducial of the first cardiac signal segment. The measured time duration can be representative of the time from the earliest activation time of one or more of the ventricles to a local ventricle activation time at least one of the electrodes of the first set of electrodes.

In some examples, at least one electrode of the first set of electrodes is configured (e.g., shaped and sized) for placement in an LV and the fiducial identified in the first cardiac signal segment is indicative of LV activation that is local to the at least one electrode of the first set of electrodes. The site activation timer circuit 530 determines a time duration between the onset of the Q-wave and LV local activation.

In some examples, at least one electrode of the first set of electrodes is configured for placement in an RV and the fiducial identified in the second cardiac signal segment is indicative of RV activation that is local to the at least one electrode of the first set of electrodes. The site activation timer circuit 530 determines a time duration between the onset of the Q-wave and RV local activation.

The second set of electrodes can be implantable electrodes or skin surface electrodes. If the second set of electrodes includes skin surface electrodes, the system 500 can be included in an external device (such as a pacing system analyzer (PSA) device) that includes the first cardiac signal sensing circuit 505, the second cardiac signal sensing circuit 520, and the processor circuit 510. The first cardiac signal sensing circuit can be electrically connectable to implantable electrodes and the first cardiac signal can be sensed as an intracardiac electrogram. The second cardiac signal sensing circuit can be electrically connectable to the skin surface electrodes and the second cardiac signal segment can be sensed as an electrocardiograph (ECG) signal.

In some examples, the first cardiac signal sensing circuit 505 can be included in an implantable device, and the second cardiac signal sensing circuit 520 and processor circuit 510 can be included in the external device. The processor circuit 510 can be communicatively coupled to a communication circuit configured to communicate information with the implantable device, such as by wireless telemetry. The first cardiac signal segment can be communicated from the implantable device to the external device.

If the second set of electrodes is implantable, the first and second cardiac signal sensing circuits can be included in an implantable device. The implantable device may be a diagnostic device or a device that provides therapy to the subject (e.g., an ICD or a pacemaker). Both of the first and second cardiac signal segments can be sensed as intracardiac electrograms. In some examples, the processor circuit 510 is included in the implantable device and the indication of local ventricular activation can be communicated to a separate device. In some examples, the processor circuit is included in the external device and the sensed first and second cardiac signal segments are communicated to external device for processing. In some examples, at least one electrode of the second set of electrodes is included in a shock channel of the implantable device. In some examples, at least one electrode of the second set of electrodes is included in a pacing channel of the implantable device.

In some examples, at least one electrode of the first set of electrodes is configured for placement in a LV and the fiducial identified in the first cardiac signal segment is indicative of LV activation that is local to the at least one electrode of the first set of electrodes. Additionally, at least one electrode of the second set of electrodes is configured for placement in an RV. The peak detector circuit 515 identifies, in the second cardiac signal segment, a fiducial indicative of RV activation that is local to at least one of the second set of electrodes. As with the first fiducial, the fiducial in the second cardiac signal segment includes a first large positive or negative peak greater than a specified percentage of a maximum peak of the second cardiac signal segment. The site activation timer circuit 530 determines a time duration between the fiducial in the second cardiac signal segment and the fiducial in the first cardiac signal segment (e.g., an RV-LV interval).

There may be latency between sensing of the cardiac signals. For instance, there may be a time delay in sensing of the first cardiac signal segment using implantable electrodes and a different time delay in sensing of the second cardiac signal segment using skin surface electrodes. This can result in inaccurate measurements of the timing intervals described. Thus, in some examples, the site activation timer circuit 530 adjusts the time duration by a specified latency value representative of latency of signal sensing between the first and second sets of electrodes. In certain examples, the specified latency value includes a value representative of a central tendency (e.g., an average value or median value) of a variable latency measured between cardiac signals sensed using the first cardiac signal sensing circuit and the second cardiac signal sensing circuit. In certain examples, the specified latency value includes a value representative of a central tendency of a variable measured signal noise due to one or both of the first cardiac signal sensing circuit and the second cardiac signal sensing circuit. The adjusted time duration is then provided to the user or process.

Knowledge of local ventricular activation can provide information regarding optimum lead placement in one or both ventricles. Additionally, information related to local ventricular activation may also be useful in identifying patients most likely to respond well to CRT. Therefore, measurements of local ventricular activation are useful information concerning a patient's cardiac health that can be provided to a physician or other care giver.

ADDITIONAL NOTES AND EXAMPLES

Example 1 includes subject matter (such as system) comprising a first cardiac signal sensing circuit configured to sense a first cardiac signal segment using a first set of electrodes connectable to the first cardiac signal sensing circuit, wherein the first cardiac signal segment is sensed over a cardiac cycle, and a processor circuit that is communicatively coupled to the first cardiac signal sensing circuit. The processor circuit includes a peak detector circuit configured to identify, in the first cardiac signal segment, a fiducial indicative of ventricular activation that is local to at least one electrode of the first set of electrodes, wherein the fiducial includes a first positive or negative peak with an amplitude that is greater than a specified percentage of a maximum peak amplitude of the first cardiac signal segment. The processor circuit can be configured to provide an indication of local ventricular activation to at least one of a user or process.

In Example 2, the subject matter of Example 1 can optionally include at least one electrode of the first set of electrodes configured for placement in a left ventricle (LV) and the fiducial identified in the first cardiac signal segment is indicative of LV activation that is local to the at least one electrode of the first set of electrodes. The system can optionally include a second cardiac signal sensing circuit configured to sense a second cardiac signal segment using a second set of electrodes, wherein at least one electrode of the second set of electrodes is configured for placement in a right ventricle (RV). The peak detector circuit can optionally by configured to identify, in the second cardiac signal segment, a fiducial indicative of RV activation that is local to at least one of the second set of electrodes, wherein the fiducial in the second cardiac signal segment includes a first positive or negative peak with an amplitude greater than a specified percentage of a maximum peak amplitude of the second cardiac signal segment. The processor circuit can optionally include a site activation timer circuit configured to determine a time duration between the fiducial in the second cardiac signal segment and the fiducial in the first cardiac signal segment, and the processor circuit can be configured to provide the determined time duration to the at least one of a user or process.

In Example 3, the subject matter of one or any combination of Examples 1 and 2 can optionally include a second cardiac signal sensing circuit configured to sense a second cardiac signal segment using a second set of electrodes, wherein at least one electrode of the second set of electrodes is different from the first set of electrodes, and wherein the second cardiac signal segment includes a QRS complex. The processor circuit can optionally include a Q-wave identification circuit configured to identify an onset of a Q-wave in a QRS complex sensed during the same cardiac cycle as the fiducial in the first cardiac signal segment, and a site activation timer circuit configured to determine a time duration between onset of the Q-wave and the identified fiducial of the first cardiac signal segment. The processor circuit is configured to provide the determined time duration to the at least one of a user or process.

In Example 4, the subject matter of one or any combination of Examples 1-3 can optionally include at least one electrode of the first set of electrodes configured for placement in an LV and the fiducial identified in the first cardiac signal segment is indicative of LV activation that is local to the at least one electrode of the first set of electrodes, and the site activation timer circuit can be configured to determine a time duration between the onset of the Q-wave and LV local activation.

In Example 5, the subject matter of one or any combination of Examples 1-4 can optionally include at least one electrode of the first set of electrodes configured for placement in an RV and the fiducial identified in the second cardiac signal segment is indicative of RV activation that is local to the at least one electrode of the first set of electrodes. The site activation timer circuit can be configured to determine a time duration between the onset of the Q-wave and RV local activation.

In Example 6, the subject matter of one or any combination of Examples 1-5 can optionally include a site activation timer circuit configured to adjust the time duration by a specified latency value representative of latency of signal sensing between the first and second sets of electrodes. The specified latency value can includes a value representative of at least one of a central tendency of a variable latency measured between cardiac signals sensed using the first cardiac signal sensing circuit and the second cardiac signal sensing circuit, or a central tendency of measured signal noise due to one or both of the first cardiac signal sensing circuit and the second cardiac signal sensing circuit.

In Example 7, the subject matter of one or any combination of Examples 1-6 can optionally include a processor circuit is configured to generate an indication of prospective responsiveness to cardiac resynchronization therapy (CRT) based on the determined time duration, and provide the indication to at least one of a user or process.

In Example 8, the subject matter of one or any combination of Examples 1-7 can optionally include the system being included in a pacing system analyzer (PSA) device that includes the first and second cardiac signal sensing circuits and the processor circuit. The first cardiac signal sensing circuit can be electrically connectable to implantable electrodes and the second cardiac signal sensing circuit is electrically connectable to skin surface electrodes.

In Example 9, the subject matter of one or any combination of Examples 1-8 can optionally include the first cardiac signal sensing circuit being included in an implantable device, and the second cardiac signal sensing circuit and processor circuit being included in an external device. The processor circuit can be communicatively coupled to a communication circuit configured to communicate information with the implantable device, and the first cardiac signal segment can be communicated from the implantable device to the external device.

In Example 10, the subject matter of one or any combination of Examples 1-9 can optionally include the first and second cardiac signal sensing circuits being included in an implantable device, and the processor circuit being included in an external device. The first and second cardiac signal sensing circuits are electrically connectable to implantable electrodes, and the processor circuit can be communicatively coupled to a communication circuit configured to communicate information with the implantable device. The first cardiac signal segment and the second cardiac signal segment can be communicated from the implantable device to the external device.

In Example 11, the subject matter of one or any combination of Examples 1-10 can optionally include at least one electrode of the second set of electrodes being included in a shock channel of the implantable device.

In Example 12, the subject matter of one or any combination of Example 1-11 can optionally include at least one electrode of the second set of electrodes being included in a pacing channel of the implantable device.

Example 13, can include subject matter, or can optionally be combined with the subject matter of one or any combination of Examples 1-12 to include subject matter (such as a method, a means for performing acts, or a machine-readable medium including instructions that, when performed by the machine, cause the machine to perform acts) comprising sensing a first cardiac signal segment using a first set of electrodes connectable to the medical device, wherein the first cardiac signal segment is sensed over a cardiac cycle, identifying, in the first cardiac signal segment and by the medical device, a fiducial indicative of ventricular activation that is local to at least one electrode of the first set of electrodes, wherein the fiducial includes a first positive or negative peak having an amplitude greater than a specified percentage of a maximum peak amplitude of the first cardiac signal segment, and providing an indication of local ventricular activation to at least one of a user or process.

In Example 14, the subject matter of Example 13 can optionally include sensing a second cardiac signal segment using a second set of electrodes during the same cardiac cycle as the fiducial identified in the first cardiac signal segment (the second cardiac signal segment can include a QRS complex, and at least one electrode of the second set of electrodes is different from the first set of electrodes), identifying an onset of a Q-wave of the QRS complex, determining, by the medical device, a time duration between the onset of the Q-wave and the fiducial of the first cardiac signal segment, and providing the determined time duration to at least one of a user or process.

In Example 15, the subject matter of one or any combination of Examples 13 and 14 can optionally include identifying a fiducial indicative of left ventricular (LV) activation that is local to at least one electrode of the first set of electrodes, and determining a time duration between the onset of the Q-wave and LV activation.

In Example 16, the subject matter of one or any combination of Examples 13-15 can optionally include identifying a fiducial indicative of right ventricular (RV) activation that is local to at least one electrode of the first set of electrodes, and determining a time duration between the onset of the Q-wave and RV activation.

In Example 17, the subject matter of one or any combination of Examples 13-16 can optionally include adjusting the determined time duration by a specified latency value representative of latency of signal sensing between the first and second sets of electrodes, and providing the adjusted time duration to the at least one of the user or process.

In Example 18, the subject matter of one or any combination of Examples 13-17 can optionally include one or both of adjusting the determined time duration using a value representative of a central tendency of a variable latency measured between cardiac signals sensed using the first set of electrodes and cardiac signals sensed using the second set of electrodes, and adjusting the determined time duration using a value representative of a central tendency of measured variable signal noise due to cardiac signal sensing circuits associated with one or both of the first and second sets of electrodes.

In Example 19, the subject matter of one or any combination of Examples 13-18 can optionally include identifying a first fiducial indicative of LV local activation, sensing a second cardiac signal segment using a second set of electrodes during the same cardiac cycle as the fiducial identified in the first cardiac signal segment, wherein at least one electrode of the second set of electrodes is different from the first set of electrodes, identifying a second fiducial in the second cardiac signal segment, wherein the second fiducial is indicative of RV activation local to at least one electrode of the second set of electrodes, and wherein the fiducial in the second cardiac signal segment includes a first positive or negative peak having an amplitude greater than a specified percentage of a maximum peak amplitude of the second cardiac signal segment, determining, by the medical device, a time duration between the second fiducial indicative of RV local activation and the first fiducial indicative of LV local activation, and providing the determined time duration to at least one of a user or process.

In Example 20, the subject matter of one or any combination of Examples 13-19 can optionally include generating, using the medical device, an indication of prospective responsiveness to cardiac resynchronization therapy (CRT) based on the indication of local ventricular activation, and providing the indication of prospective responsiveness to at least one of a user or process.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." In the event of inconsistent usages between this document and documents incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
a first cardiac signal sensing circuit configured to sense a first cardiac signal segment using a first set of electrodes connectable to the first cardiac signal sensing circuit, wherein the first cardiac signal segment is sensed over a cardiac cycle;
a processor circuit communicatively coupled to the first cardiac signal sensing circuit, wherein the processor circuit includes a peak detector circuit configured to:
identify, in the first cardiac signal segment, a maximum peak of a cardiac cycle of the first cardiac signal segment,
identify, within the same cardiac cycle, a first positive or negative peak having an amplitude that is greater than a specified percentage of the identified maximum peak, and
indicate the identified positive or negative peak as a fiducial indicative of ventricular activation that is local to at least one electrode of the first set of electrodes, wherein the processor circuit is configured to provide an indication of local ventricular activation to at least one of a user or process.

2. The system of claim 1,
wherein at least one electrode of the first set of electrodes is configured for placement in a left ventricle (LV) and the fiducial identified in the first cardiac signal segment is indicative of LV activation that is local to the at least one electrode of the first set of electrodes, and
wherein the system includes:
a second cardiac signal sensing circuit configured to sense a second cardiac signal segment using a second set of electrodes, wherein at least one electrode of the second set of electrodes is configured for placement in a right ventricle (RV),
wherein the peak detector circuit is configured to identify, in the second cardiac signal segment, a fiducial indicative of RV activation that is local to at least one of the second set of electrodes, wherein the fiducial in the second cardiac signal segment includes a first positive or negative peak with an amplitude greater than a specified percentage of a maximum peak amplitude of the second cardiac signal segment,
wherein the processor circuit includes a site activation timer circuit configured to determine a time duration between the fiducial in the second cardiac signal segment and the fiducial in the first cardiac signal segment, and
wherein the processor circuit is configured to provide the determined time duration to the at least one of a user or process.

3. The system of claim 1, including:
a second cardiac signal sensing circuit configured to sense a second cardiac signal segment using a second set of electrodes, wherein at least one electrode of the second set of electrodes is different from the first set of electrodes, and wherein the second cardiac signal segment includes a QRS complex, and
wherein the processor circuit includes:
a Q-wave identification circuit configured to identify an onset of a Q-wave in a QRS complex sensed during the same cardiac cycle as the fiducial in the first cardiac signal segment; and
a site activation timer circuit configured to determine a time duration between onset of the Q-wave and the identified fiducial of the first cardiac signal segment, and
wherein the processor circuit is configured to provide the determined time duration to the at least one of a user or process.

4. The system of claim 3,
wherein at least one electrode of the first set of electrodes is configured for placement in an LV and the fiducial identified in the first cardiac signal segment is indicative of LV activation that is local to the at least one electrode of the first set of electrodes, and wherein the site activation timer circuit is configured to determine a time duration between the onset of the Q-wave and LV local activation.

5. The system of claim 3, wherein at least one electrode of the first set of electrodes is configured for placement in an RV and the fiducial identified in the second cardiac signal segment is indicative of RV activation that is local to the at least one electrode of the first set of electrodes, and wherein the site activation timer circuit is configured to determine a time duration between the onset of the Q-wave and RV local activation.

6. The system of claim 3, wherein the site activation timer circuit is configured to adjust the time duration by a specified latency value representative of latency of signal sensing between the first and second sets of electrodes, wherein the specified latency value includes a value representative of at least one of:

a central tendency of a variable latency measured between cardiac signals sensed using the first cardiac signal sensing circuit and the second cardiac signal sensing circuit, or a central tendency of measured signal noise due to one or both of the first cardiac signal sensing circuit and the second cardiac signal sensing circuit.

7. The system of claim 3, wherein the processor circuit is configured to:

generate an indication of prospective responsiveness to cardiac resynchronization therapy (CRT) based on the determined time duration; and provide the indication to at least one of a user or process.

8. The system of claim 3, wherein the system is included in a pacing system analyzer (PSA) device that includes the first and second cardiac signal sensing circuits and the processor circuit, wherein the first cardiac signal sensing circuit is electrically connectable to implantable electrodes and the second cardiac signal sensing circuit is electrically connectable to skin surface electrodes.

9. The system of claim 3, wherein the first cardiac signal sensing circuit is included in an implantable device, and the second cardiac signal sensing circuit and processor circuit are included in an external device, wherein the processor circuit is communicatively coupled to a communication circuit configured to communicate information with the implantable device, and wherein the first cardiac signal segment is communicated from the implantable device to the external device.

10. The system of claim 3, wherein the first and second cardiac signal sensing circuits are included in an implantable device, and the processor circuit are included in an external device, wherein the first and second cardiac signal sensing circuits are electrically connectable to implantable electrodes, wherein the processor circuit is communicatively coupled to a communication circuit configured to communicate information with the implantable device, and wherein the first cardiac signal segment and the second cardiac signal segment are communicated from the implantable device to the external device.

11. The system of claim 10, wherein at least one electrode of the second set of electrodes is included in a shock channel of the implantable device.

12. The system of claim 10, wherein at least one electrode of the second set of electrodes is included in a pacing channel of the implantable device.

13. A method of operating a medical device, the method comprising:

sensing a first cardiac signal segment using a first set of electrodes connectable to the medical device, wherein the first cardiac signal segment is sensed over a cardiac cycle;

identifying, in the first cardiac signal segment and by the medical device, a maximum peak of a cardiac cycle of the first cardiac signal segment, identifying, with in the same cardiac cycle, a first positive or negative peak having an amplitude greater than a specified percentage of the indentified maximum peak; and generating an indication of the indentified positive or negative peak as a fiducial indicative of ventricular activation that is local to at least one electrode of the first set of electrodes and providing the indication of local ventricular activation to at least one of a user or process.

14. The method of claim 13, including:

sensing a second cardiac signal segment using a second set of electrodes during the same cardiac cycle as the fiducial identified in the first cardiac signal segment, wherein the second cardiac signal segment includes a QRS complex, and wherein at least one electrode of the second set of electrodes is different from the first set of electrodes;

identifying an onset of a Q-wave of the QRS complex;

determining, by the medical device, a time duration between the onset of the Q-wave and the fiducial of the first cardiac signal segment; and wherein providing the indication includes providing the determined time duration to at least one of a user or process.

15. The method of claim 14, wherein identifying a fiducial indicative of ventricular activation includes identifying a fiducial indicative of left ventricular (LV) activation that is local to at least one electrode of the first set of electrodes, and wherein determining a time duration between the onset of the Q-wave and the fiducial of the first cardiac signal segment includes determining a time duration between the onset of the Q-wave and LV activation.

16. The method of claim 14, wherein identifying a fiducial indicative of ventricular activation includes identifying a fiducial indicative of right ventricular (RV) activation that is local to at least one electrode of the first set of electrodes, and wherein determining a time duration between the onset of the Q-wave and the fiducial of the first cardiac signal segment includes determining a time duration between the onset of the Q-wave and RV activation.

17. The method of claim 14, including:

adjusting the determined time duration by a specified latency value representative of latency of signal sensing between the first and second sets of electrodes, and wherein providing the determined time duration includes providing the adjusted time duration to the at least one of the user or process.

18. The method of claim 17, wherein adjusting the determined time duration includes at least one of:

adjusting the determined time duration using a value representative of a central tendency of a variable latency measured between cardiac signals sensed using the first set of electrodes and cardiac signals sensed using the second set of electrodes, or adjusting the determined time duration using a value representative of a central tendency of measured variable signal noise due to cardiac signal sensing circuits associated with one or both of the first and second sets of electrodes.

19. The method of claim 13, wherein identifying the fiducial in the first cardiac signal segment includes identifying a first fiducial indicative of LV local activation, and wherein the method further includes:

sensing a second cardiac signal segment using a second set of electrodes during the same cardiac cycle as the fiducial identified in the first cardiac signal segment, wherein at least one electrode of the second set of electrodes is different from the first set of electrodes;

identifying a second fiducial in the second cardiac signal segment, wherein the second fiducial is indicative of RV activation local to at least one electrode of the second set of electrodes, and wherein the fiducial in the second cardiac signal segment includes a first positive or negative peak having an amplitude greater than a specified percentage of a maximum peak amplitude of the second cardiac signal segment; and determining, by the medical device, a time duration between the second fiducial indicative of RV local activation and the first fiducial indicative of LV local activation, and wherein providing the indication includes providing the determined time duration to at least one of a user or process.

20. The method of claim 13, including:

generating, using the medical device, an indication of prospective responsiveness to cardiac resynchronization therapy (CRT) based on the indication of local ventricular activation; and providing the indication of prospective responsiveness to at least one of a user or process.

* * * * *